(12) United States Patent
Durgin

(10) Patent No.: US 8,105,392 B2
(45) Date of Patent: Jan. 31, 2012

(54) PYLORIC OBESITY VALVE

(75) Inventor: Russ Durgin, Bellingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 625 days.

(21) Appl. No.: 11/594,406

(22) Filed: Nov. 8, 2006

(65) Prior Publication Data

US 2008/0109087 A1    May 8, 2008

(51) Int. Cl.
*A61F 2/04* (2006.01)
*A61B 19/00* (2006.01)

(52) U.S. Cl. ............... 623/23.68; 128/898; 606/153

(58) Field of Classification Search ....... 623/23.65–23.7; 604/8–10; 128/898; 606/153
See application file for complete search history.

(56) References Cited

U.S. PATENT DOCUMENTS

| | | |
|---|---|---|
| 4,503,569 A | 3/1985 | Dotter |
| 4,580,568 A | 4/1986 | Gianturco |
| 4,732,152 A | 3/1988 | Wallsten et al. |
| 4,733,665 A | 3/1988 | Palmaz |
| 4,856,516 A | 8/1989 | Hillstead |
| 4,886,062 A | 12/1989 | Wiktor |
| 5,314,473 A | 5/1994 | Godin |
| 5,861,036 A | 1/1999 | Godin |
| 6,290,666 B1 * | 9/2001 | Devonec ............... 623/1.16 |
| 6,540,789 B1 | 4/2003 | Silverman et al. |
| 6,675,809 B2 * | 1/2004 | Stack et al. ............ 128/898 |
| 6,764,518 B2 | 7/2004 | Godin |
| 6,802,868 B2 | 10/2004 | Silverman et al. |
| 2002/0035396 A1 | 3/2002 | Heath |
| 2003/0009236 A1 | 1/2003 | Godin |
| 2003/0209835 A1 * | 11/2003 | Chun et al. ............ 264/339 |
| 2004/0133147 A1 * | 7/2004 | Woo ...................... 604/9 |
| 2004/0158331 A1 * | 8/2004 | Stack et al. ........... 623/23.65 |
| 2005/0085923 A1 | 4/2005 | Levine et al. |
| 2005/0096750 A1 | 5/2005 | Kagan et al. |
| 2005/0149200 A1 | 7/2005 | Silverman et al. |
| 2005/0192614 A1 | 9/2005 | Binmoeller |
| 2005/0228415 A1 | 10/2005 | Gertner |
| 2005/0228504 A1 * | 10/2005 | Demarais ............. 623/23.65 |
| 2009/0259236 A2 * | 10/2009 | Burnett et al. ........ 606/153 |

FOREIGN PATENT DOCUMENTS

EP    1508312 A1    2/2005

* cited by examiner

*Primary Examiner* — Suzette J Gherbi
(74) *Attorney, Agent, or Firm* — Vidas, Arrett & Steinkraus

(57) ABSTRACT

The pyloric obesity valve includes a tubular valve body having proximal and distal ends. The valve body has an intermediate section which is between the proximal and distal ends. The proximal end is enlarged transversely relative to the intermediate section. The valve body has an inner surface and a lumen. The inner surface which is within the intermediate section has a cross-sectional area which is smaller than a cross-sectional area of the inner surface which coincides with the proximal end to resist a flow through the lumen of the valve body from the proximal end to the intermediate section.

20 Claims, 7 Drawing Sheets

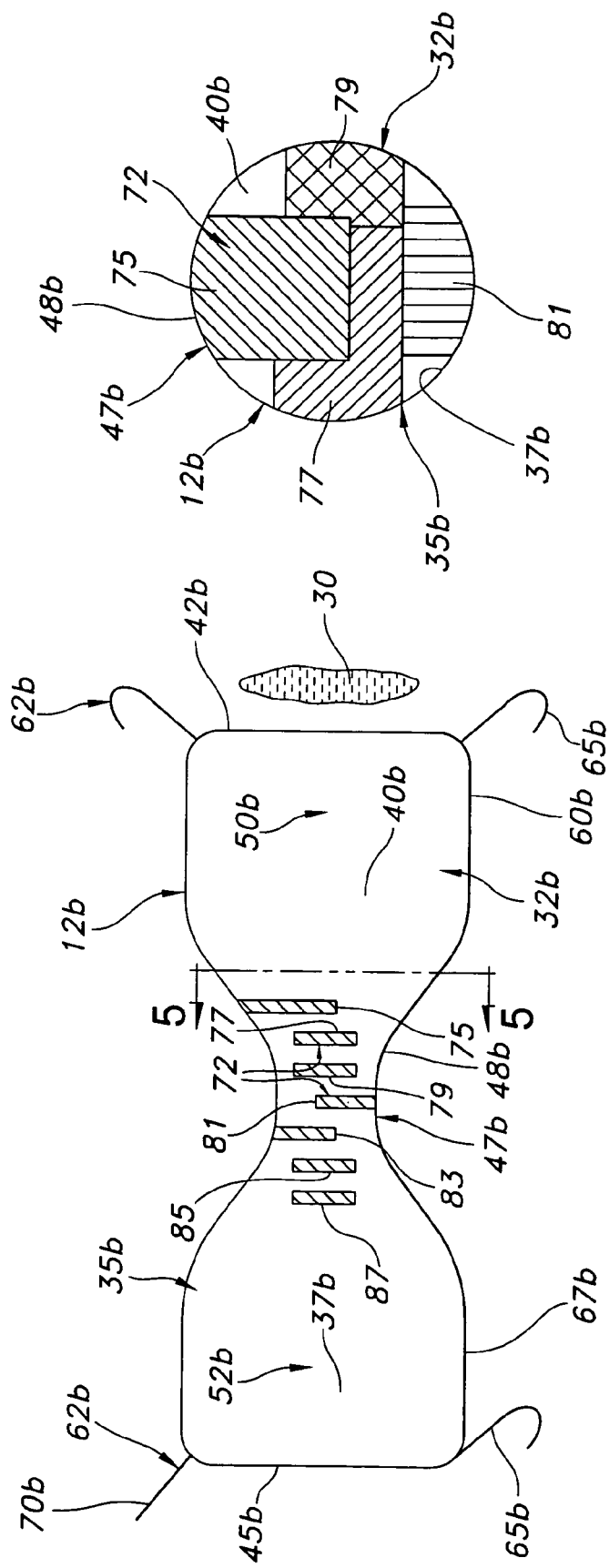

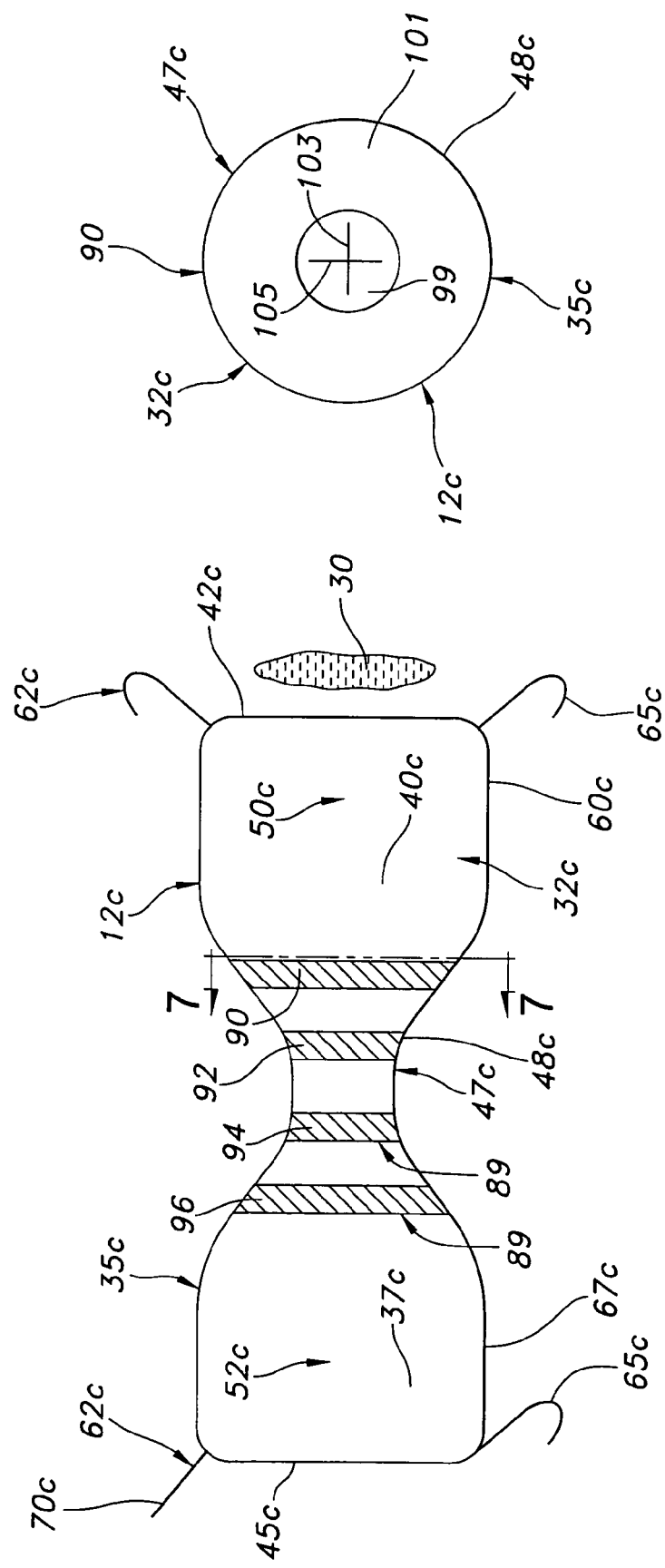

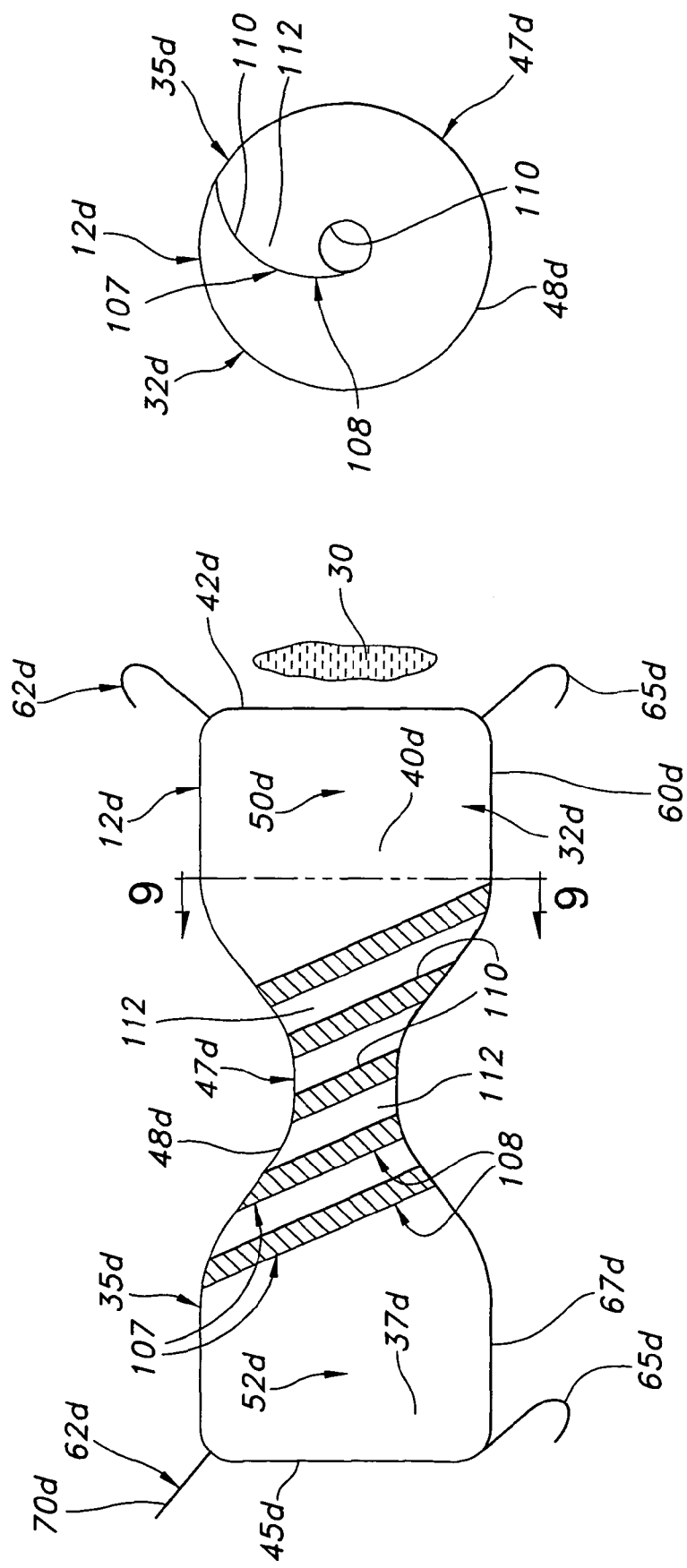

PYLORIC OBESITY VALVE

FIELD OF THE INVENTION

The present invention relates generally to implants in the pylorus for treating obesity and, more specifically, to a pyloric obesity valve which extends through the pylorus to delay emptying of the stomach.

BACKGROUND OF THE INVENTION

The incidence of obesity and its associated health-related problems has become significant. The causes of obesity may involve a complex interplay of genetic, environmental, psycho-behavioral, endocrine, metabolic, cultural, and socio-economic factors. Severe obesity is frequently associated with significant comorbid medical conditions, including coronary artery disease, hypertension, type II diabetes mellitus, gallstones, nonalcoholic steatohepatitis, pulmonary hypertension, and sleep apnea.

Current treatments for obesity range from diet, exercise, behavioral modification, and pharmacotherapy to various types of surgery, with varying risks and efficacy. In general, nonsurgical treatments, although less invasive, achieve only relatively short-term and limited weight loss in most patients. Surgical treatments include gastroplasty to restrict the capacity of the stomach to hold large amounts of food, such as by stapling or "gastric banding". Other surgical procedures include gastric bypass and gastric "balloons" which, when deflated, may be inserted into the stomach and then are distended by filling with saline solution.

The need exists for low cost, less invasive interventions for the treatment of obesity, including morbid obesity.

SUMMARY OF THE INVENTION

The pyloric obesity valve of the present invention includes a tubular valve body having proximal and distal ends. The valve body has an intermediate section which is between the proximal and distal ends. The valve body is sized for implanting within the pylorus such that the proximal end is upstream and the distal end is downstream of the pylorus. The intermediate section crosses the pylorus when the valve body is implanted within the pylorus. The proximal end is enlarged transversely relative to the intermediate section to a dimension which is larger than a maximum opening of the pylorus. The valve body has an entry section between the intermediate section and proximal end. The entry section has an outer surface which is shaped such that, when the valve body is implanted within the pylorus, the outer surface is then substantially in direct contact with an inner surface of the stomach which is adjacent to the pylorus. The valve body has an inner surface and a lumen. The lumen has a transverse boundary which is defined by the inner surface of the valve body. The inner surface which is within the intermediate section has a cross-sectional area which is smaller than a cross-sectional area of the inner surface which coincides with the proximal end to resist a flow through the lumen of the valve body from the proximal end to the intermediate section.

The pyloric obesity valve, when implanted so to extend through the pylorus, obstructs and impedes the passage of chyme from the stomach through the pylorus into the duodenum. Chyme is the partially digested food which flows into the duodenum from the stomach. The duodenum is the longitudinal portion of the small intestine which contains the proximal end thereof. The obstruction and impediment provided by the pyloric obesity valve delays the emptying of the chyme in the stomach through the pylorus into the duodenum. Delaying this emptying of the stomach will typically prolong the satiation of the patient which results from the chyme in the stomach. Consequently, the onset of hunger which normally results from the stomach being empty of chyme is delayed. The intake of food by the patient which results from hunger is consequently delayed. Absent some other reason for eating, the patient will normally experience longer time periods between eating which will typically result in a reduction in the daily food absorption by the patient. The longer durations between eating would not appear to result in the patient desiring larger quantities of food when the hunger returns. Consequently, the longer durations between eating should contribute to significant weight loss in the patient.

These and other features of the invention will be more fully understood from the following description of specific embodiments of the invention taken together with the accompanying drawings.

BRIEF DESCRIPTION OF THE DRAWINGS

In the drawings:

FIG. 4 is longitudinal cross-sectional view of a further alternative embodiment of the pyloric obesity valve of FIG. 1, the pyloric obesity valve being shown as removed from the alimentary canal and as having transverse baffles secured within the valve body;

FIG. 5 is a transverse cross-sectional view of the pyloric obesity valve in the plane indicated by line 5-5 of FIG. 4, the baffles being shown as longitudinally and transversely offset relative to the valve body;

FIG. 6 is a longitudinal cross-sectional view of a further alternative embodiment of the pyloric obesity valve of FIG. 1, the pyloric obesity valve being shown as removed from the alimentary canal and as having transverse membranes secured within the valve body;

FIG. 7 is a transverse cross-sectional view of the pyloric obesity valve in the plane indicated by line 7-7 of FIG. 6, one of the membranes being shown as having slits therein;

FIG. 8 is a longitudinal cross-sectional view of a further alternative embodiment of the pyloric obesity valve of FIG. 1, the pyloric obesity valve being shown as removed from the alimentary canal and as having an internal thread on the inner surface of the valve body;

FIG. 9 is a transverse cross-sectional view of the pyloric obesity valve in the plane indicated by line 9-9 of FIG. 8, the internal thread being shown as transversely overlapping.

Corresponding reference characters indicate corresponding parts throughout the several views of the drawings.

DETAILED DESCRIPTION OF THE INVENTION

Figure 1:
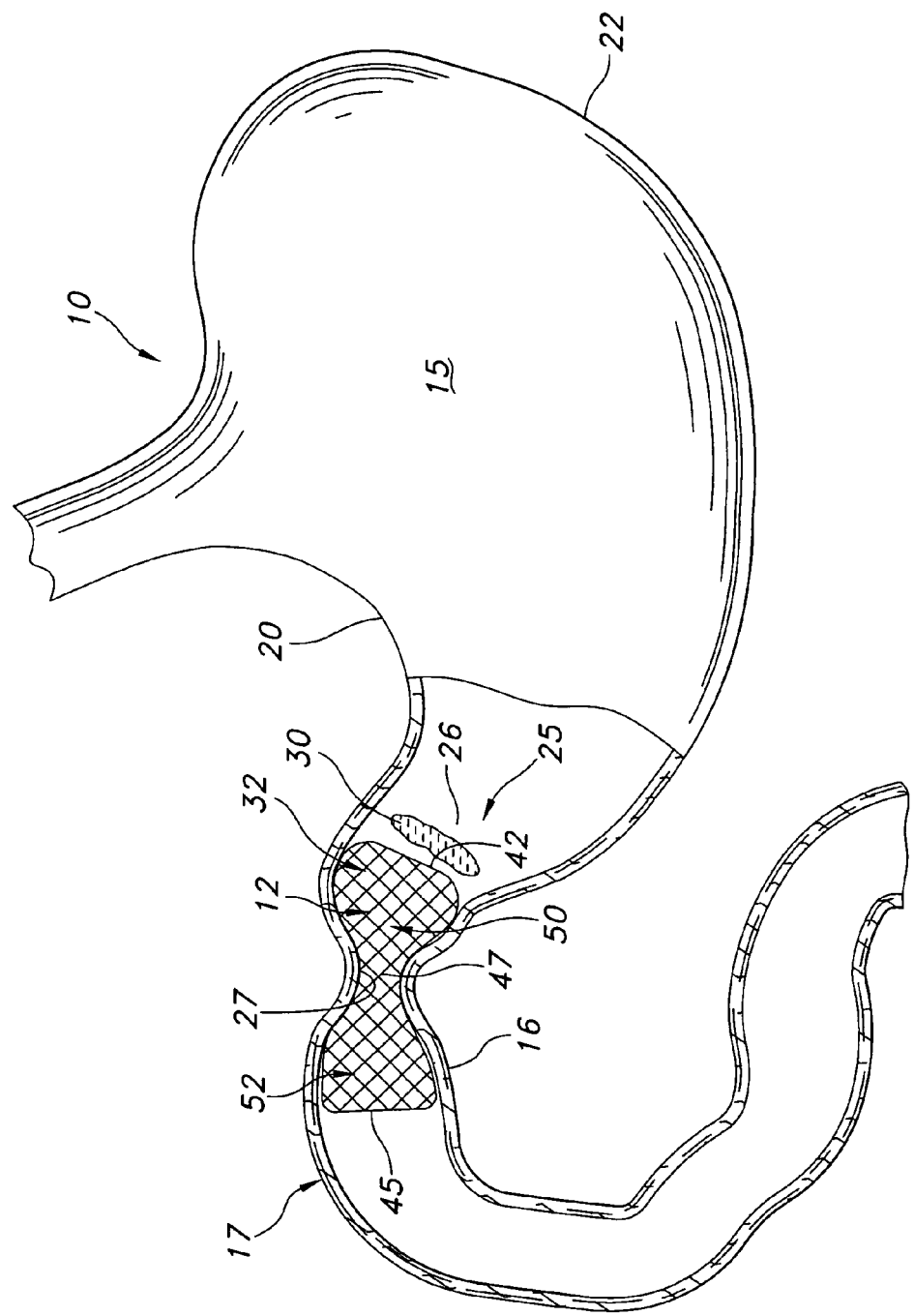
FIG. 1 is an anatomical elevational view of a pylorus and the adjacent portions of the stomach and duodenum, the walls of the pylorus, stomach and duodenum being broken away to show a pyloric obesity valve in accordance with the present invention.

Referring to the drawings and more particularly to FIG. 1, a central portion of the alimentary canal 10 in which the pyloric obesity valve 12 is located is illustrated. This portion of the alimentary canal 10 includes the stomach 15 and duodenum 17. The stomach 15 has lesser and greater curves 20, 22, and a pyloric canal 25 which has an inner surface 26. The pyloric canal 25 leads to the duodenal bulb 16 of the duodenum 17 by way of the pylorus 27, which may be referred to alternatively as the gastric outlet or pyloric opening. The pylorus 27 forms the distal aperture of the stomach 15 and has an enclosing circular layer of muscle which is normally contracted to close the aperture but which relaxes to provide an open but restrictive passage. Although subject to substantial variation in different individuals, the pylorus 27 has a maximum open diameter of about 2 cm. and the duodenum 17 has a diameter which typically is about 18 to 20 mm. in a representative patient. The chyme 30 passes from the pyloric canal 25 through the pylorus 27 into the duodenal bulb 16 of the duodenum 17. The duodenum 17, including the duodenal bulb 16, is the proximate segment of the small intestine. The duodenal bulb 16 has an inner surface 31.

Figure 2:
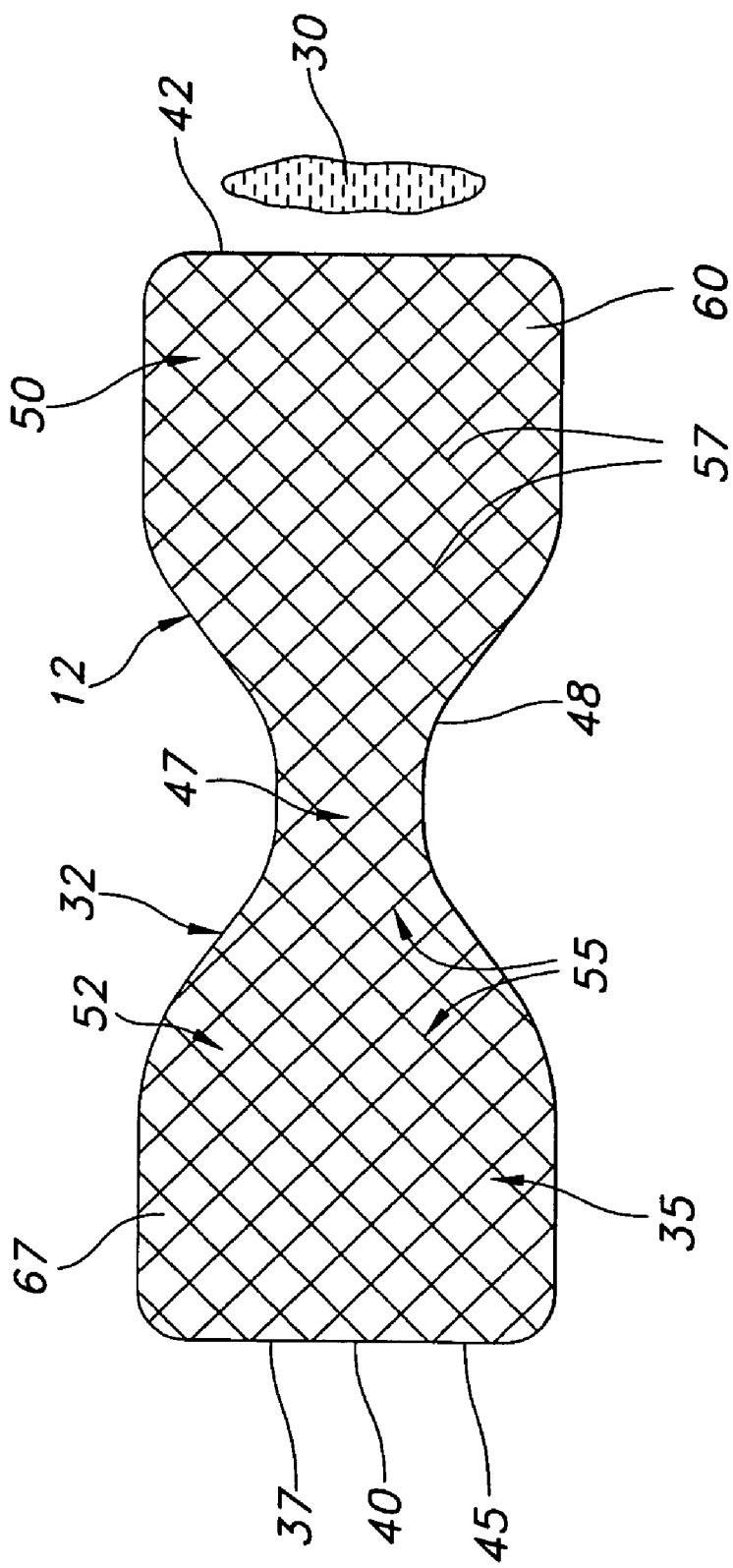
FIG. 2 is an elevational side view of the pyloric obesity valve of FIG. 1, the pyloric obesity valve being shown as removed from the alimentary canal and as having a stent in the valve body.

The pyloric obesity valve 12 is located within the pyloric canal 25, pylorus 27, and duodenal bulb 16, as shown in FIG. 1. The pyloric obesity valve 12 is shown in FIG. 2 before insertion into the pyloric canal 25, pylorus 27, and duodenal bulb 16. The pyloric obesity valve 12 includes a valve body 32 which has outer and inner surfaces 35, 37. The inner surface 37 defines a transverse boundary of a lumen 40 of the valve body 32. The valve body 32 has proximal and distal ends 42, 45 and an intermediate section 47 which is between the proximal and distal ends. The intermediate section 47 has an outer surface 48 which coincides with a longitudinal portion of the outer surface 35. The valve body 32 has an entry section 50 between the intermediate section 47 and proximal end 42. The entry section 50 has an outer surface 60 which coincides with a longitudinal portion of the outer surface 35. The valve body 32 has a discharge section 52 between the intermediate section 47 and distal end 45. The discharge section 52 has an outer surface 67 which coincides with a longitudinal portion of the outer surface 35.

The proximal and distal ends 42, 45 are enlarged transversely relative to the intermediate section 47. The cross-sections of the entry and discharge sections 50, 52 increase in size with increasing longitudinal separation from the intermediate section 47. In an alternative embodiment, it is possible for a longitudinal portion of the entry section 50 to have a constant cross-section. Also, in alternative embodiments, it is possible for a longitudinal portion or the entire length of the discharge section 52 to have a constant cross-section. Additionally, in an alternative embodiment, the cross-section of the distal end 45 may be the same as the cross-section of the intermediate section 47. The valve body 32 typically has an annular cross-section. Alternative embodiments of the pyloric obesity valve 12 are possible in which the valve body 32 has a non-annular cross-section, such as the cross-section of the valve body 32 as manufactured being elliptical or having multiple radii with different angular positions within the valve body.

The valve body 32 includes a tubular stent 55 which has a plurality of elongate structural members 57. The structural members 57 are arranged in a crossing pattern. The structural members 57 may be wires, the cross-sections of which may be round, rectangular, square or numerous other geometric shapes.

The stent 55, including the structural members 57, may be formed of materials such as nitinol, elgiloy, stainless steel or cobalt chromium, including NP35N. Additionally, the stent 55, including the structural members 57, may be formed of materials such as stainless steel, platinum, gold, titanium and other biocompatible metals, as well as polymeric stents. Polymeric stents may be provided, such as POLYFLEX® stents which are made by the Boston Scientific Corporation. Also, the stent 55, including the structural members 57, may be formed of materials including cobalt-based alloy such as Elgiloy, platinum, gold, titanium, tantalum, niobium, and combinations thereof and other biocompatible materials, as well as polymers. The stent 55, including the structural members 57, may be formed of any biocompatible polymer including, but not limited to, PET, PTFE, PE, and nylon. Also, the stent 55, including the structural members 57, may be formed of biocompatible ceramics, such as structurally or as coatings. Additionally, the structural members 57 which have an inner core formed of tantalum gold, platinum, iridium, or a combination thereof, and an outer cladding of nitinol to provide composite members for improved radio-opacity or visibility. Examples of such composite members are disclosed in U.S. Patent Application Publication No. 2002/0035396, the entire contents of which are hereby incorporated by reference herein. The structural members 57 may be formed of combinations of more than one metal, more than one polymer, and metals and polymers.

The stent 55 may have various embodiments. For example, the stent 55 may be self-expanding or expandable by a balloon. The stent 55 may include one or more coiled stainless steel springs, helically wound coil springs including a heat-sensitive material, or expanding stainless steel stents formed of stainless steel wire in a zig-zag pattern. The stent 55 may be made with braided, woven, knitted or otherwise twisted filaments. The stent 55 may include joined filaments which may be joined by welding, soldering, adhesives and the like. The stent 55 may be formed from a tube which is cut mechanically or by lasers and the like. The stent 55 may be molded, spun, or created in layers (lithography) especially if polymeric. The stent 55 may be capable of radially contracting or expanding, such as by radial or circumferential distension or deformation. The stent 55 may be self-expanding, such as a stent which is mechanically urged to radially expand, and a stent which expands at one or more specific temperatures as a result of the memory properties of the stent material for a specific configuration. Such a stent 55 may include nitinol material for providing radial expansion thereof both by mechanical urging, or by the memory properties of the nitinol based on one or more specific temperatures. The stent 55 may have any shape memory material including metals and polymers. The stent 55 may include one or more of the stents disclosed in U.S. Pat. Nos. 4,503,569, 4,733,665, 4,856,516, 4,580,568, 4,732,152, and 4,886,062, the entire contents of each of which are hereby incorporated by reference herein.

The pyloric obesity valve 12 may include a tubular cover which is secured to the outer surface of the stent 55. The cover may be formed of various biocompatible materials. For example, the cover may be a PERMALUME® covering which is secured to the stent 55, which is a stent constituted by the WALLSTENT® RX Biliary Endoprosthesis, both of which are made by the Boston Scientific Corporation. The PERMALUME® covering is formed of polyurethane. Alternatively, the cover may be formed of expanded polytetrafluoroethylene (ePTFE). The cover, and possibly the stent 55, may be an elastomer such as silicone, c-flex, polyurethane, PEBAX® copolymer, or other known biocompatible materials. The cover could be made of the PERMALUME® material which is used in combination with the WALLSTENT®. The cover may have other materials and configurations. For example, the longitudinal center and end portions of the cover may be an elastomer with a shore hardness of 10 to 100 Shore A. The shore hardness of the elastomer of the longitudinal center and end portions of the cover may also be specified in the shore D scale. The center portion is softer and able to close with the sphincter pressure of the pylorus 27 while the relatively harder end portions better retain the shape thereof to match the anatomical pockets. The stent 55 and a cover may be attached to one another by various processes, depending upon the materials of the cover and stent. For example, a cover may be insert molded over the stent 55, which may also be formed of a polymeric elastomer or silicone. Alternatively, the cover and stent 55 may be secured to one another by an interference fit between the two structures. Alternatively, a shorter term implant may be provided by a coating on the outer surface of the stent 55 to facilitate removal thereof from the tissue. The cover may be added to the stent 55 by dipping the stent in a liquid polymer. Alternatively, the cover material may be sprayed on, or molded onto the stent 55. In a further alternative embodiment, the cover may be wrapped around, woven on, spun around, knitted on, and adhesed to the stent 55. A further alternative embodiment provides for the implantation of the stent 55 which does not have a cover on the outer surface thereof to facilitate tissue in-growth or adhesions for a more permanent implant.

In alternative embodiments, the valve body 32 may be a polymer sleeve. The valve body 32 may be formed of biocompatible materials, such as polymers which may include fillers such as metals, carbon fibers, glass fibers or ceramics. Such polymers may include olefin polymers, polyethylene, polypropylene, polyvinyl chloride, polytetrafluoroethylene which is not expanded, fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk may be included in the valve body 32.

The valve body 32 may be treated with anti-thrombogenic agents (such as heparin, heparin derivatives, urokinase, and PPack (dextrophenylalanine proline arginine chloromethylketone)), anti-proliferative agents (such as enoxaprin, angiopeptin, or monoclonal antibodies capable of blocking smooth muscle cell proliferation, hirudin, and acetylsalicylic acid), anti-inflammatory agents (such as dexamethasone, prednisolone, corticosterone, budesonide, estrogen, sulfasalazine, and mesalamine), antineoplastic/antiproliferative/ anti-miotic agents (such as paclitaxel, 5-fluorouracil, cisplatin, vinblastine, vincristine, epothilones, endostatin, angiostatin and thymidine kinase inhibitors), anesthetic agents (such as lidocaine, bupivacaine, and ropivacaine), anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides), vascular cell growth promotors (such as growth factor inhibitors, growth factor receptor antagonists, transcriptional activators, and translational promotors), vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin), cholesterol-lowering agents, vasodilating agents, and agents which interfere with endogenous vasoactive mechanisms. The valve body 32 may be treated with agents which are particular to digestion or to promote sphincter activity.

The valve body 32 has a cross-section which varies relative to the longitudinal axis thereof. This is a result of the proximal and distal ends 42, 45 being enlarged relative to the intermediate section 47 and the tapering of the cross-sections of the entry and discharge sections 50, 52 between the proximal and distal ends, respectively, and the intermediate section. The reduced cross-section of the intermediate section 47 provides for a narrowing of the longitudinal portion of the lumen 40 therein. This narrowing of the lumen 40 provides resistance to the flow of the chyme 30 therein from the proximal end 42 to the intermediate section 47. The distal end 45 may be enlarged transversely to a lesser degree relative to the proximal end 42, as shown in FIGS. 1 and 2. In an alternative embodiment of the valve body 32, the distal end 45 may be enlarged transversely to different degrees relative to the degree of transverse enlargement shown in FIGS. 1 and 2. In a further alternative embodiment of the valve body 32, the distal end 45 may have generally the same transverse dimension as the intermediate section 47.

The valve body 32 is sized for implanting within the pylorus 27 by inserting the distal end 45 in a downstream direction through the pylorus. Such insertion provides for the proximal end 42 to be upstream and the distal end 45 to be downstream of the pylorus 27, as shown in FIG. 1. The insertion of the distal end 45 through the pylorus 27 results in the outer surface 48 of the intermediate section 47 crossing the pylorus. Also, the intermediate section 47 may be in direct contact with the pylorus 27. The outer surface 60 of the entry section 50 is preferably shaped such that, when the valve body 32 is implanted within the pylorus 27, the outer surface 60 is in substantially direct contact with the inner surface 26 of the pyloric canal 25 of the stomach 15 which is adjacent to the pylorus. The inner surface 26 is adjacent to the pylorus 27. The outer surface 60 of the entry section 50 is held against the inner surface 26 by the stent 55. The shape of the outer surface 35 before insertion of the valve body 32 into the pyloric canal 25, pylorus 27, and duodenal bulb 16, as shown in FIG. 2, may be different from the shape of the outer surface 35 after the insertion of the valve body 32, as shown in FIG. 1. This may be provided by the cross-section of the outer surface 35 being larger than the corresponding cross-sections of the pyloric canal 25, pylorus 27, and duodenal bulb 16 before the insertion of the valve body 32 therein, and the valve body being formed of a compressible material. Consequently, insertion of the valve body 32 into the pyloric canal 25, pylorus 27, and duodenal bulb 16 results in radial compression of the valve body such that the outer surface 35 is urged by the radial expansion of the valve body into direct contact with the anatomy of the pyloric canal 25, pylorus 27, and duodenal bulb 16, as shown in FIG. 1. The direct contact between the valve body 32 and the anatomy of the pyloric canal 25, pylorus 27, and duodenal bulb 16 may be facilitated by the increased cross-sections of the entry and discharge sections 50, 52 relative to the intermediate section 47 and, in some anatomies, by the valve body having a non-annular cross-section.

In an alternative embodiment, the respective cross-sections of the intermediate and discharge sections 47, 52 may be the same to provide a radial clearance between the discharge section and duodenal bulb 16.

The transverse enlargements of the proximal end 42 and entry section 50 are greater than the maximum transverse opening of the pylorus 27. These enlargements provide resistance to downstream displacement of the valve body 32 relative to the pylorus 27 to maintain the valve body therein. The lumen 40 and the substantially direct contact of the outer surface 60 with the inner surface 26 results in the chyme 30 which is in the pyloric canal 25 flowing through the lumen 40 into the duodenal bulb 16 of duodenum 17. The substantially direct contact of the outer surface 60 with the inner surface 26 also prevents the chyme 30 from being trapped between the surfaces 26, 60 and possibly leaking through the surface 26. The direction of the flow of the chyme 30 through the lumen 40 and the narrowing thereof within the intermediate section 47 forces the entry section 50 against the inner surface 26 to resist upstream displacement of the valve body 32 relative to the pylorus 27 to maintain the valve body therein.

The implantation provided by the forcing of the entry section 50 against the inner surface 26 as a result of the flow of the chyme 30 through the lumen 40 provides sufficient resistance to downstream displacement of the valve body 32 relative to the pylorus 27 to maintain the valve body therein. This allows for the variations in the transverse dimensions of the distal end 45 and discharge section 52. These variations are possible since the distal end 45 and discharge section 52 are not required to implant the valve body 32 within the pylorus 27. The implantation of the pyloric obesity valve 12 results in the outer surface 48 of the intermediate section 47 being in direct contact with the pylorus 27. The insertion of the valve body 32 through the pylorus 27 in the distal direction results in the outer surface 67 of the discharge section 52 being adjacent to the inner surface 31 of the duodenal bulb 16 of the duodenum 17, as shown in FIG. 1. The inner surface 31 is adjacent to the pylorus 27. Preferably, the outer surface 67 is in direct contact with the inner surface 31, as shown in FIG. 1. Alternative embodiments of the valve body 32 are possible in which a transverse clearance is provided between the outer and inner surfaces 67, 31.

The pyloric obesity valve 12 may be dislodged from the implantation thereof in the pyloric canal 25, pylorus 27 and duodenal bulb 16 by displacing the valve body 32 in an upstream direction relative to the pylorus. The displacement of the valve body 32 in the upstream direction is sufficient to retract the intermediate section 47 from within the pylorus 27.

Figure 3:
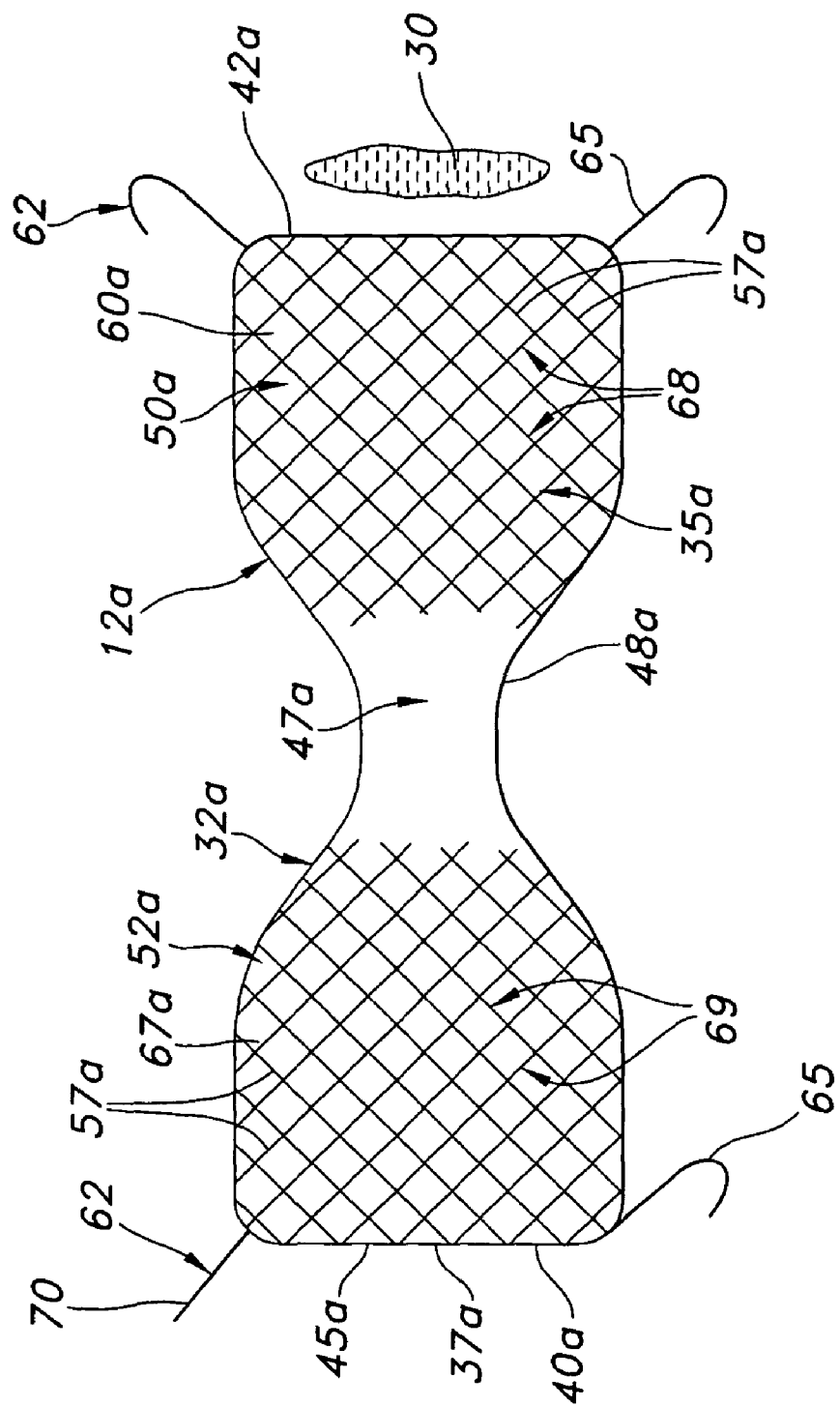
FIG. 3 is an elevational side view of an alternative embodiment of the pyloric obesity valve of FIG. 1, the pyloric obesity valve being shown as removed from the alimentary canal and as having stents in the entry and discharge sections.

An alternative embodiment of the pyloric obesity valve 12a is shown in FIG. 3. Parts illustrated in FIG. 3 which correspond to parts illustrated in FIGS. 1 and 2 have, in FIG. 3, the same reference numeral as in FIGS. 1 and 2 with the addition of the suffix "a". In this alternative embodiment, the entry and discharge sections 50a, 52a of the valve body 32a each include corresponding tubular stents 68, 69. The stents 68, 69 may have structures which correspond to the stent 55. The intermediate section 47a does not include a stent. Consequently, the entry and discharge sections 50a, 52a are stiffer transversely relative to the transverse flexibility of the intermediate section 47a.

The pyloric obesity valve 12a has an anchor structure 62 which includes a pair of hooks 65 which are attached to the outer surface 60a of the entry section 50a, as shown in FIG. 2.

The hooks 65 have longitudinal positions relative to the valve body 32a which are adjacent to the proximal end 42a. The hooks 65 have opposing transverse positions relative to the valve body 32a. The hooks 65 each have a distal curvature relative to the valve body 32a such that the ends thereof point in a generally distal direction. Alternative embodiments of the anchor structure 62 are possible which include different numbers of the hooks 65 and attachment thereof to different locations on the outer surface 35a of the valve body 32a. For example, a hook 65 may be attached to the distal end 45a, as shown in FIG. 3. Alternative embodiments of the anchor structure 62 are possible which include more than one hook 65 each of which is attached to the valve body 32a adjacent to the distal end 45a. In such alternative embodiments of the anchor structure 62, the hooks 65 preferably have a distal curvature relative to the valve body 32a, although other directions of curvature of the hooks 65 are possible.

The anchor structure 62 includes a stake 70 which is attached to the outer surface 67a of the discharge section 52a, as shown in FIG. 3. The stake 70 has a longitudinal position relative to the valve body 32a which is adjacent to the distal end 45a. The stake 70 may have opposing transverse positions relative to the valve body 32a. The stake 70 has a distal inclination relative to the valve body 32a. The stake 70 may be straight, as shown in FIG. 3, or, in an alternative embodiment, curved. Alternative embodiments of the anchor structure 62 are possible which include more than one stake 70 each of which has a longitudinal position relative to the valve body 32a which is adjacent to the distal end 45a. Alternative embodiments of the anchor structure 62 are possible which include different numbers of the stakes 70 and attachment thereof to different locations on the outer surface 35a of the valve body 32a. In such alternative embodiments of the anchor structure 62, the stakes 70 preferably have a distal inclination relative to the valve body 32a, although other inclinations of the stakes 70 are possible. Alternative embodiments of the anchor structure 62 may have only hooks 65, only stakes 70, neither or both.

The hooks 65 and stakes 70 resist migration of the valve body 32a in the distal direction relative to the pyloric canal 25, pylorus 27, and duodenal bulb 16. This resistance results from the distal direction of the peristalsis relative to the pyloric canal 25, pylorus 27, and duodenal bulb 16.

During implantation of the pyloric obesity valve 12a including the insertion of the valve body 32a through the pylorus 27 in the downstream direction, the direct contact of the outer surface 60a with the inner surface 26 of the pyloric canal 25 results in the hooks 65 being implanted in the inner surface 26. Such implantation also results in the stakes 70 being implanted in the inner surface 31 of the duodenal bulb 16 of the duodenum 17.

The distal curvature of the hooks 65 and distal inclination of the stakes 70 facilitate the implantation thereof in the inner surfaces 26, 31, respectively, as a result of the insertion of the valve body 32a through the pylorus 27 in the downstream direction. Such displacement of the valve body 32a in the downstream direction may be the result of an initial insertion of the pyloric obesity valve 12a through the mouth of the patient. Such oral insertion of the pyloric obesity valve 12a may be advantageous by not requiring a surgical incision, such as through the abdomen, for implantation of the pyloric obesity valve.

The implantation of the pyloric obesity valve 12a results in the outer surface 48a of the intermediate section 47a being in direct contact with the pylorus 27. The increased flexibility of the intermediate section 47a relative to the entry and discharge sections 50a, 52a provides for the conformance thereof to the pylorus 27 during contraction and dilation thereof which may occur as a natural result of digestion.

The dislodging of the pyloric obesity valve 12a including the retraction of the valve body 32a through the pylorus 27 in the upstream direction is sufficient to dislodge the hooks 65 from the inner surface 26 of the pyloric canal 25 of the stomach 15. Such displacement further provides for the stakes 70 to be dislodged from the inner surface 31 of the duodenal bulb 16 of the duodenum 17. The distal curvature of the hooks 65 and the distal inclination of the stake 70, facilitate dislodging thereof from the inner surfaces 26, 31, respectively, by displacement of the valve body 32a in the upstream direction relative to the pylorus 27.

The dislodging of the pyloric obesity valve 12a from the implantation thereof by displacement of the valve body 32a in the upstream direction may ultimately result in the removal of the pyloric obesity valve through the mouth of the patient. Such oral removal of the pyloric obesity valve 12a may be advantageous by not requiring a surgical incision, such as through the abdomen, for dislodging the implantation of the pyloric obesity valve.

An alternative embodiment of the pyloric obesity valve 12b is shown in FIGS. 4 and 5. Parts illustrated in FIGS. 4 and 5 which correspond to parts illustrated in FIGS. 1 and 2 have, in FIGS. 4 and 5, the same reference numeral as in FIGS. 1 and 2 with the addition of the suffix "b". In this alternative embodiment, a flow restrictor 72 is secured to the inner surface 37b of the valve body 32b. The flow restrictor 72 includes baffles 75, 77, 79, 81, 83, 85, 87, each of which is secured to the inner surface 37b of the valve body 32b. As shown in FIG. 4, the baffles 75, 77, 79, 81, 83, 85, 87 are within the intermediate section 47b. The baffles 75, 77, 79, 81, 83, 85, 87 are formed of a compressible material which conforms to the periodically reduced transverse dimension of the pylorus 27. This periodically reduced transverse dimension typically results from the contraction of the sphincter in the pylorus 27 during peristalsis.

In an alternative embodiment of the flow restrictor 72, the baffles 75, 77, 79, 81, 83, 85, 87 may be within the entry and discharge sections 50b, 52b, and fewer or no baffles in the intermediate section 47b. A possible advantage of such an embodiment is that the degree of compression required of the baffles 75, 77, 79, 81, 83, 85, 87 in the entry and discharge sections 50b, 52b is less than the degree of compression which is typically required of the baffles which are located in the intermediate section 47b. This results from the longitudinal offset of the entry and discharge sections 50b, 52b relative to the pylorus 27. The longitudinal offset reduces the possible transverse contraction of the entry and discharge sections 50b, 52b which may result from the contraction of the sphincter in the pylorus 27.

The baffles 75, 77, 79, 81, 83, 85, 87 are longitudinally offset relative to the valve body 32b such that the baffles are each longitudinally separated from the adjacent baffles, as shown in FIG. 4. The baffles 75, 77, 79, 81 are secured to sections of the inner surface 37b of the valve body 32b which are transversely offset relative thereto. Consequently, the sections of the inner surface 37b to which adjacent baffles, such as the baffles 75, 77, are secured are transversely offset relative to the valve body 32b, as shown in FIG. 5. The baffles 83, 85, 87 are secured to sections of the inner surface 37b which correspond transversely to the sections of the inner surface 37b to which are connected the baffles 75, 77, 79. Consequently, the baffles 83, 85, 87 are offset transversely relative to the valve body 32b.

The baffles 75, 77, 79, 81, 83, 85, 87 are sized and secured to a section of the inner surface 37b such that a transverse clearance is provided between each baffle and the inner surface 37b. Consequently, the chyme 30 may flow longitudinally between each of the baffles 75, 77, 79, 81, 83, 85, 87 and the longitudinally corresponding portions of the inner surface 37b. Such flow of the chyme 30 is resisted by the baffles 75, 77, 79, 81, 83, 85, 87 as a result of the reduction in the transverse area through which the chyme may flow resulting from the surface area of the baffles. Additional resistance to the flow of the chyme 30 is provided by the transverse offset of the baffles 75, 77, 79, 81, 83, 85, 87 which requires the chyme to flow in a serpentine direction as a result of the transverse offset of the attachments of the baffles to the inner surface 37b. Alternative embodiments of the flow restrictor 72 are possible which have different numbers of baffles, such as the baffles 75, 77, 79, 81, 83, 85, 87. Further alternative embodiments of the flow restrictor 72 are possible which have structures for resisting the flow of the chyme 30 within the lumen 40b where such structures are different from the baffles 75, 77, 79, 81, 83, 85, 87. Further alternative embodiments of the pyloric obesity valve 12b are possible which have more than a single flow restrictor 72.

An alternative embodiment of the pyloric obesity valve 12b is shown in FIGS. 6 and 7. Parts illustrated in FIGS. 6 and 7 which correspond to parts illustrated in FIGS. 1 and 2 have, in FIGS. 6 and 7, the same reference numeral as in FIGS. 1 and 2 with the addition of the suffix "c". In this alternative embodiment, a flow restrictor 89 is secured to the inner surface 37c of the valve body 32c. The flow restrictor 72c may include the transverse membranes 90, 92, 94, 96 each of which has a periphery the entire length of which is secured to the inner surface 37c of the valve body 32c. The membranes 90, 92, 94, 96 are each substantially impermeable. Alternative embodiments of the flow restrictor 89 are possible which have one or more membranes, such as the membranes 90, 92, 94, 96.

The membrane 90 has an inner section 99 which is circular and contained within an outer section 101. The outer section 101 is annular and has an outer peripheral which is secured to the inner surface 37c. The inner and outer sections 99, 101 are each flexible longitudinally relative to the valve body 32c. The longitudinal flexibility of the inner section 99 is greater than the longitudinal flexibility of the outer section 101. Consequently, the application of a uniform longitudinal force to the inner and outer sections 99, 101 will produce a longitudinal deflection of the inner section which is greater than the longitudinal deflection of the outer section. The respective longitudinal flexibilities of the inner and outer sections 99, 101 may be provided by the thickness of the inner section being smaller than the thickness of the outer section. The thicknesses of the inner and outer sections 99, 101 may be uniform in the transverse direction. Alternatively, the thicknesses of the inner and outer sections 99, 101 may vary in the transverse direction to provide tapered thicknesses thereof. In an alternative embodiment of the flow restrictor 89, the membranes 90, 92, 94, 96 may each be substantially inflexible longitudinally relative to the valve body 32c.

The flow restrictor 89 includes one or more orifices which, in the pyloric obesity valve 12c shown in FIG. 7, are provided by horizontal and vertical slits 103, 105. The horizontal and vertical slits 103, 105 intersect with one another at a location which coincides with the center of the inner section 99. The membranes 92, 94, 96 each have one or more orifices formed therein. The orifices in the membranes 92, 94, 96 may be provided by slits corresponding to the horizontal and vertical slits 103, 105. Alternatively, the orifices of the membranes 92, 94, 96 may have configurations which differ from the horizontal and vertical slits 103, 105. Alternative embodiments of the orifices in the membranes 90, 92, 94, 96 may be provided by a small hole, a slit, a slot, a cross, such as the horizontal and vertical slits 103, 105, or any combination thereof.

The membranes 90, 92, 94, 96 and the corresponding orifices therein provide resistance to the flow of the chyme 30 through the lumen 40c by requiring the chyme to flow through the relatively small cross-sectional areas of the orifices. This resistance to the flow of the chyme 30 may be controllably adjusted such as by varying the longitudinal flexibility of the section of the membrane in which the one or more orifices are formed. A reduction in the resistance to the flow of the chyme 30 may, for example, be provided by increasing the longitudinal flexibility of the inner section 99. Increasing the longitudinal flexibility of the inner section 99 will reduce the longitudinal force required to longitudinally deflect the portions of the inner section which are contiguous with the horizontal and vertical slits 103, 105. Longitudinal deflection of these portions of the inner section 99 typically increases the cross-sectional area of the horizontal and vertical slits 103, 105 which reduce the resistance provided by the membrane 90 to the flow of the chyme 30. Conversely, decreasing the longitudinal flexibility of the inner section 99 will typically increase the resistance to the flow of the chyme 30 which is provided by the membrane 90. In alternative embodiments, the membranes 90, 92, 94, 96 can be configured to promote or restrict flow through the lumen 40c. The membranes 90, 92, 94, 96 may have a uniform thickness or tapered thickness, may be rounded, or may have other profiles. The membranes 90, 92, 94, 96 may have different characteristics relative to one another.

An alternative embodiment of the pyloric obesity valve 12d is shown in FIG. 8. Parts illustrated in FIG. 8 which correspond to parts illustrated in FIGS. 1 and 2 have, in FIG. 8, the same reference numeral as in FIGS. 1 and 2 with the addition of the suffix "d". In this alternative embodiment, a flow restrictor 107 is secured to the inner surface 37d of the valve body 32d. The flow restrictor 107 includes an internal thread 108 having rotational and longitudinal orientations which are offset relative to the valve body 32d. These offset rotational and longitudinal orientations provide for the internal thread 108 to be helical in a valve body 32d which has an annular cross-section, as shown in FIG. 8. The internal thread 108 has a sufficiently large transverse dimension such that an internal edge 110 thereof has longitudinal portions which transversely overlap one another relative to the valve body 32d. This transverse overlap results in the passage through the longitudinal portion of the lumen 40d, within which the internal thread 108 is located, being substantially limited to a channel 112 within the internal thread 108. The configuration of the internal thread 108 has similarities to an auger in that material, such as the chyme 30, is displaced longitudinally through the channel 112. The formation of the internal thread 108 on the inner surface 37d provides the flow restrictor 107 with a correspondence to an internal auger. In alternative embodiments of the pyloric obesity valve 12d, the flow restrictor 107 may have more than one of the internal threads 108. In a further alternative embodiment of the pyloric obesity valve 12d, the internal thread 108 may have a sufficiently limited transverse dimension to provide a transverse clearance between the internal edge 110 such that the longitudinal portions of the internal edge 110 do not transversely overlap one another relative to the valve body 32d. The transverse dimension of the internal thread 108 is sufficient to resist the flow of the chyme 30 through the lumen 40d.

Figure 10:
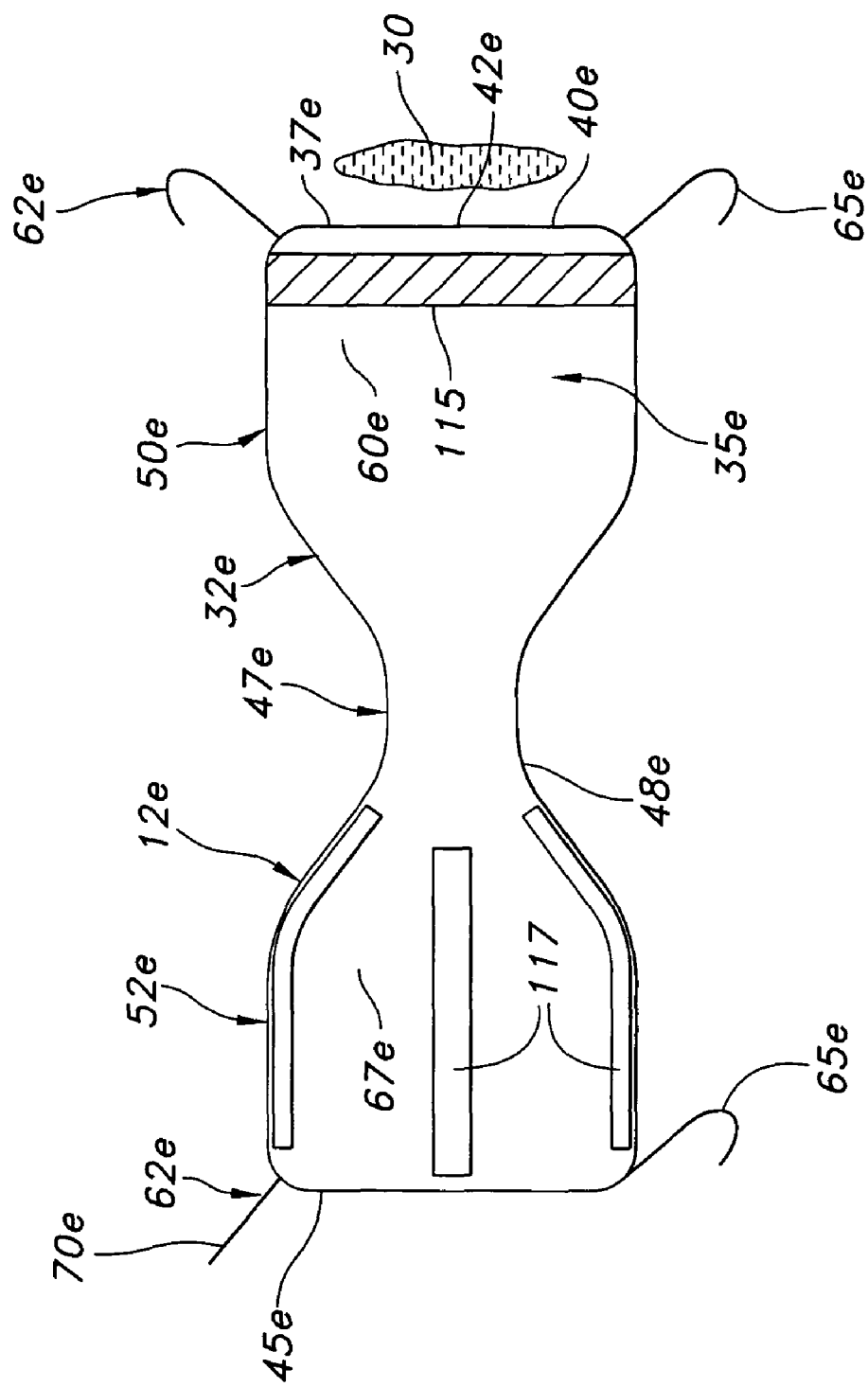
FIG. 10 is an elevational side view of a further alternative embodiment of the pyloric obesity valve of FIG. 1, the pyloric obesity valve being shown as removed from the alimentary canal and as having longitudinal and transverse supports on the valve body.

An alternative embodiment of the pyloric obesity valve 12e is shown in FIG. 10. Parts illustrated in FIG. 10 which correspond to parts illustrated in FIGS. 1 and 2 have, in FIG. 10, the same reference numeral as in FIGS. 1 and 2 with the addition of the suffix "e". In this alternative embodiment, the pyloric obesity valve 12e includes an elongate transverse support member 115 which is secured to the entry section 50e in adjacent relation to the proximal end 42e. The support member 115 may be circular for attachment to the outer surface 60e which has a cross-section which is circular. The support member 115 is continuous. In an alternative embodiment of the pyloric obesity valve 12e, the support member 115 may include arcuate sections the ends of which may abut one another or be transversely offset from one another. Also, such arcuate sections of the support member 115 may be longitudinally offset from one another. In a further alternative embodiment of the pyloric obesity valve 12e, more than one support member 115 may be secured to the entry section 50e.

The pyloric obesity valve 12e includes elongate longitudinal support members 117 which are secured to the discharge section 52e and which are transversely offset relative to one another by generally equal dimensions. The support members 117 are continuous. In an alternative embodiment of the pyloric obesity valve 12e, the support members 117 may include longitudinal sections the ends of which may abut one another or be longitudinally offset from one another. In further alternative embodiments of the pyloric obesity valve 12e, different numbers of the support members 117, including a single one thereof, may be secured to the discharge section 52e.

Alternative embodiments of the pyloric obesity valve 12e are possible in which one or more transverse support members 115 are secured to the discharge section 52e and one or more longitudinal support members 117 are secured to the entry section 50e. In further alternative embodiments of the pyloric obesity valve 12e, the transverse and longitudinal support members 115, 117 may both be secured to the entry section 50e. Also, the transverse and longitudinal support members 115, 117 may both be secured to the discharge section 52e. Additionally, the transverse and longitudinal support members 115, 117 may be located at either or both of the proximal and distal ends 42e, 45e.

Alternative embodiments of the pyloric obesity valve 12e are possible which include one or more support structures secured to the entry section 50e which maintain the entry section in an open configuration to allow the flow of the chyme 30 through the proximal end 42e into the lumen 40e. Resistance to the flow of the chyme 30 through the lumen 40e is provided by the reduction in the cross-section of the portion of the lumen which is within the intermediate section 47e relative to the cross-section of the portion of the lumen which is within the entry section 50e. This reduction in the respective cross-sections may be provided by a taper between the entry and intermediate sections 50e, 47e. The one or more support structures which are secured to the entry section 50e allows the entry section and intermediate section 47e to be formed of flexible material, such as a membrane, since the entry section is held in an open configuration by the one or more support structures. Such an assembly may resemble a windsock which is held open at the top thereof. The one or more support structures which are secured to the entry section 50e may be provided by struts which are inclined relative to the longitudinal axis of the valve body 32e, a stent, a stent component, or a transverse support member 115 which is defined by a metal or material hoop. The entry section 50e to which the one or more support structures are secured may be included in a valve body 32e having an intermediate section 47e which is flexible and does not have a stent secured thereto. Such a valve body 32e may have a discharge section 52e which has an enlarged cross-section relative to the cross-section of the intermediate section 47e and a taper which corresponds to the taper of the entry section 50e except for the longitudinal inclination thereof which is the mirror-image of the longitudinal inclination of the taper of the entry section 50e. A stent may be secured to the discharge section 52e. The valve body 32e in these alternative embodiments may be a molded tube, and may include inner flow restrictions, such as the flow restrictor 72e.

An alternative embodiment of the pyloric obesity valve 12 is a valve structure for implanting in or around a sphincter in a body lumen. An example of such a body lumen is the pyloric canal 25, and the lumens in the pylorus 27 and duodenal bulb 16 in fluid communication therewith. The corresponding sphincter for this body lumen is the pylorus 27. Other body lumens have corresponding sphincters, in or around which the valve structure may be implanted for restricting the flow rate of fluids within the body lumens.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. A valve structure for a sphincter in a body lumen, the valve structure comprising:
    a tubular valve body having proximal and distal ends, the valve body having an intermediate section which is between the proximal and distal ends,
    the valve body having an inner surface and a lumen, the lumen having a transverse boundary which is defined by the inner surface of the valve body, the inner surface which is within the intermediate section having a cross-sectional area which is smaller than a cross-sectional area of the inner surface which coincides with the proximal end; wherein the valve structure comprises a flow restrictor comprising one or more baffles which are secured to the inner surface of the valve body, wherein the baffles are formed of a compressible material, wherein the baffles are transversely and longitudinally offset relative to the valve body; and wherein the baffles are separated from adjacent baffles by a distance.

2. A valve structure according to claim 1, the valve body being sized for implanting in or around the pylorus.

3. A valve structure according to claim 1, wherein the flow restrictor resists the flow through the lumen of the valve body.

4. A valve structure according to claim 1, wherein the distal end has a larger cross-section than the intermediate section.

5. A valve structure according to claim 1, and further comprising an elongate support member secured to the valve body.

6. A valve structure according to claim 1, wherein the valve body has an entry section between the intermediate section and proximal end, the intermediate section being more flexible transversely relative to the entry section.

7. A valve structure according to claim 1, and further comprising an anchor structure attached to an outer surface of the valve body.

8. A valve structure according to claim 7, wherein the anchor structure comprises a hook.

9. A valve structure according to claim 7, wherein the anchor structure comprises a stake.

10. A valve structure for a sphincter in a body lumen, the valve structure comprising:
    a tubular valve body having proximal and distal ends, the valve body having an intermediate section which is between the proximal and distal ends, the valve body having an inner surface and a lumen, the lumen having a transverse boundary which is defined by the inner surface of the valve body, the inner surface which is within the intermediate section having a cross-sectional area which is smaller than the cross-sectional area of the proximal end and the cross-sectional area of the distal end, wherein a flow restrictor is secured to the inner surface of the valve body, wherein the flow restrictor comprises a transverse membrane which has a periphery the entire length of which is secured to the inner surface of the valve body, and wherein one or more orifices are formed in the transverse membrane; wherein the one or more orifices comprise one or more slits.

11. A valve structure according to claim 10, wherein the membrane has one or more sections which are flexible longitudinally relative to the valve body.

12. A valve structure for a sphincter in a body lumen, the valve structure comprising:
    a tubular valve body having proximal and distal ends, the valve body having an intermediate section which is between the proximal and distal ends, the valve body having an inner surface and a lumen, the lumen having a transverse boundary which is defined by the inner surface of the valve body, the inner surface which is within the intermediate section having a cross-sectional area which is smaller than a cross-sectional area of the inner surface which coincides with the proximal end, wherein the valve body comprises a flow restrictor secured to the inner surface of the valve body, wherein the flow restrictor comprises an internal thread formed on the inner surface of the valve body.

13. A valve structure according to claim 12, wherein the internal thread has a sufficiently large transverse dimension such that an internal edge of the internal thread has longitudinal portions which transversely overlap one another relative to the valve body.

14. A method for implanting a valve structure within a pylorus, said method comprising:
    providing a valve structure including a tubular valve body having proximal and distal ends, the valve body having an intermediate section which is between the proximal and distal ends, the valve body having an inner surface and a lumen, the lumen having a transverse boundary which is defined by the inner surface of the valve body, the inner surface which is within the intermediate section having a cross-sectional area which is smaller than a cross-sectional area of the inner surface which coincides with the proximal end to resist a flow through the lumen of the valve body from the proximal end to the intermediate section;
    wherein the valve structure comprises a flow restrictor comprising one or more baffles which are secured to the inner surface of the valve body, wherein the baffles are formed of a compressible material, and wherein the baffles are transversely and longitudinally offset relative to the valve body; and
    inserting the distal end of the valve body in a downstream direction through a pylorus such that the proximal end is upstream of the pylorus and the distal end is downstream of the pylorus, and locating the intermediate section in crossing relation to the pylorus.

15. A method according to claim 14, wherein the valve structure comprises an anchor structure attached to an outer surface of the valve body, the method comprising implanting the anchor structure in an inner surface of a stomach or duodenum which is adjacent to the pylorus.

16. A method according to claim 15, wherein the anchor structure comprises a hook,
said implanting comprising implanting the hook in the inner surface of the stomach or duodenum.

17. A method according to claim 15, wherein the anchor structure comprises a stake,
said implanting comprising implanting the stake in the inner surface of the stomach or duodenum.

18. A method for implanting a valve structure within a pylorus, said method comprising:
providing a valve structure including a tubular valve body having proximal and distal ends, the valve body having an intermediate section which is between the proximal and distal ends, the valve body having an inner surface and a lumen, the lumen having a transverse boundary which is defined by the inner surface of the valve body, the inner surface which is within the intermediate section having a cross-sectional area which is smaller than a cross-sectional area of the inner surface which coincides with the proximal end to resist a flow through the lumen of the valve body from the proximal end to the intermediate section, the valve body being inserted through a pylorus;
wherein the valve structure comprises a flow restrictor comprising one or more baffles which are secured to the inner surface of the valve body, wherein the baffles are formed of a compressible material, and wherein the baffles are transversely and longitudinally offset relative to the valve body; and
displacing the valve body in an upstream direction relative to the pylorus to retract the intermediate section from within the pylorus and to dislodge the valve structure therefrom.

19. A method according to claim 18, wherein the valve structure includes an anchor structure attached to an outer surface of the valve body, the anchor structure being implanted in an inner surface of a stomach or duodenum which is adjacent to the pylorus,
the displacing further comprising displacing the valve body in an upstream direction relative to the pylorus to dislodge the anchor structure from the inner surface of the stomach or duodenum, said displacing being sufficient to retract the intermediate section from within the pylorus and to dislodge the valve structure therefrom and from the inner surface of the stomach or duodenum.

20. The valve structure of claim 1, wherein the intermediate section does not include a stent.

* * * * *